(12) United States Patent
Lv et al.

(10) Patent No.: US 12,240,822 B2
(45) Date of Patent: Mar. 4, 2025

(54) NAPHTHALENE ISOXAZOLINE COMPOUND AND APPLICATION THEREOF

(71) Applicants: SHANDONG CHENGCHUANG BLUE SEA PHARMACEUTICAL TECHNOLOGY CO., LTD., Shandong (CN); Zhitao Lv, Shandong (CN)

(72) Inventors: Zhitao Lv, Shandong (CN); Zhen Jiang, Shandong (CN); Ting Nie, Shandong (CN); Xingmin Lu, Shandong (CN); Zhongjie Liu, Shandong (CN); Songzhi Yao, Shandong (CN); Yan Cao, Shandong (CN)

(73) Assignee: SHANDONG CHENGCHUANG BLUE SEA PHARMACEUTICAL TECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 18/820,199

(22) Filed: Aug. 29, 2024

(65) Prior Publication Data

US 2024/0425468 A1 Dec. 26, 2024

Related U.S. Application Data

(63) Continuation of application No. PCT/CN2023/103946, filed on Jun. 29, 2023.

(30) Foreign Application Priority Data

Jan. 16, 2023 (CN) .......................... 202310070589.1

(51) Int. Cl.
| | | |
|---|---|---|
| C07D 261/04 | (2006.01) | |
| A01N 43/80 | (2006.01) | |
| A01P 7/02 | (2006.01) | |
| A01P 7/04 | (2006.01) | |

(52) U.S. Cl.
CPC ........... *C07D 261/04* (2013.01); *A01N 43/80* (2013.01); *A01P 7/02* (2021.08); *A01P 7/04* (2021.08)

(58) Field of Classification Search
CPC . C07D 261/04; A01P 7/04; A01P 7/02; A01N 43/80
See application file for complete search history.

(56) References Cited

U.S. PATENT DOCUMENTS

2012/0030841 A1 2/2012 Koerber et al.

FOREIGN PATENT DOCUMENTS

| CN | 101351456 A | 1/2009 |
|---|---|---|
| CN | 101815706 A | 8/2010 |
| CN | 102088857 A | 6/2011 |
| CN | 111936492 A | 11/2020 |
| WO | 2011154433 A2 | 12/2011 |
| WO | 2011157733 A2 | 12/2011 |

*Primary Examiner* — Amanda L. Aguirre
*Assistant Examiner* — Chris E Simmons
(74) *Attorney, Agent, or Firm* — Rondaus PLLC; George Liu

(57) ABSTRACT

The disclosure discloses a naphthalene isoxazoline compound and an application thereof. The compound is referred to as 4-(5-(3-chloro-5-(trifluoromethyl)phenyl)-5-(trifluoromethyl)-4,5-dihydroisoxazol-3-yl)-N-((methoxyimino)methyl)-1-naphthyl formamide, is a novel γ-aminobutyric acid (GABA) gated chloride ion channel allosteric modulator type insecticide, and can be applied to the prevention and control of various pests and/or pest mites in agriculture. Compared with commercially available agricultural insecticides, the compound has better insecticidal effects and also has a wider insecticidal range. In addition, a synthesis process for the novel compound is easy to operate and has high safety, and the compound has great application potential.

10 Claims, 2 Drawing Sheets

NAPHTHALENE ISOXAZOLINE COMPOUND AND APPLICATION THEREOF

TECHNICAL FIELD

The disclosure relates to a new naphthalene isoxazoline compound, specifically to, a naphthalene isoxazoline compound and an application thereof, belonging to the technical field of pesticide compounds.

BACKGROUND

At present, the use of insecticides to control agricultural pests is still the most effective way worldwide. Most insecticides are nerve poisons, such as ryanodine receptors, neonicotinoids, γ-aminobutyric acid receptors (GABA), and pyrethroids. In order to maintain the advantages of modern pesticides in terms of high efficiency, low toxicity, pesticide resistance, environmental friendliness, economic feasibility, etc., it is still necessary to continuously discover and develop new products, where isoxazoline compounds stand out in this situation.

The isoxazoline compounds are a type of novel insecticides that act on specific sites of ionic γ-aminobutyric acid (GABA) receptors, have the characteristics of broad spectrum, high activity, high selectivity, etc., and have better biological activity to agricultural pests in hemiptera, thysanoptera, diptera and lepidoptera, and mites. At present, products of this type of compounds that have been listed as pesticides and insecticides include fluxametamide/fluxametamide, etc.

Fluxametamide (English generic name: fluxametamide; trade name: Gracia) is an isoxazoline type insecticide and acaricide developed by Nissan Chemical Industries Co., Ltd., which is a γ-aminobutyric acid (GABA) gated chloride ion channel allosteric modulator. In the following, fluxametamide is marked as a compound C4, and the chemical structural formula of the compound C4 is as follows:

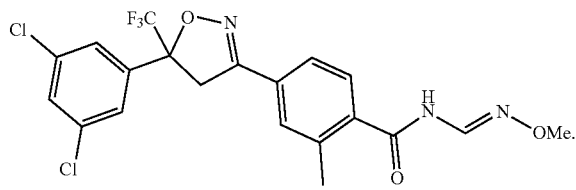 [SMILES: CO/N=C/NC(=O)c1ccc(C2=NOC(c3cc(Cl)cc(Cl)c3)(C(F)(F)F)C2)cc1C]

Fluxametamide was registered in South Korea in 2018, first listed in South Korea in the second quarter of 2018, and listed in Japan in 2019 for use in vegetables and tea trees. This product will also enter other Asian markets. The Environmental Protection Agency (EPA) plans to make a decision on the import permit for this product for tea trees before Feb. 1, 2021. Nissan Chemical predicts that the sales of fluxametamide will reach 10 billion yen. This product is mainly used for crops such as vegetables, fruit trees, cotton and tea trees to prevent and control pests and pest mites such as *thrips*, whiteflies, leaf miners, beetles, red spider mites and rust mites. At present, in agricultural production, the application of pesticides is an important means for preventing and controlling plant diseases and insect pests. However, with the repeated and extensive use of existing pesticides, coupled with some farmers' improper application of pesticides, some pests gradually have significant resistance to existing common pesticides, so the difficulty in medicament prevention and control is increasing. For this problem, developing and researching new drugs is an effective way to solve the problem of pest resistance. Therefore, the development of new high-efficiency, low-toxicity and safe insecticides for prevention and control of insect pests is of great significance.

At present, there are no insecticide products showing unexpected insecticidal effects using naphthalene isoxazoline compounds as insecticides available in agricultural chemistry.

SUMMARY

In order to overcome the above defects in the prior art, the disclosure provides a naphthalene isoxazoline compound and an application thereof.

In order to achieve the above objective, the disclosure adopts the following technical solution:

1. Disclosed is a naphthalene isoxazoline compound, or a chiral monomer or mixture thereof, or a cis-trans isomer monomer or mixture thereof, or an agrichemically acceptable salt, hydrate or solvate thereof. The compound is referred to as 4-(5-(3-chloro-5-(trifluoromethyl)phenyl)-5-(trifluoromethyl)-4,5-dihydroisoxazol-3-yl)-N-((methoxylimino)methyl)-1-naphthyl formamide, and has a structure shown in Formula (I) (hereinafter denoted as a compound A4):

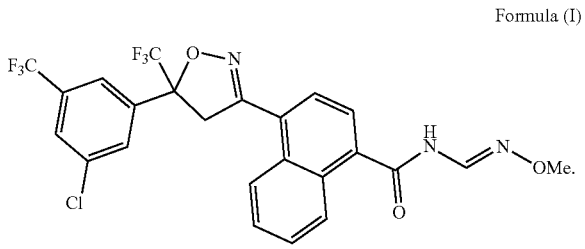 [SMILES: CO/N=C/NC(=O)c1ccc(C2=NOC(c3cc(Cl)cc(C(F)(F)F)c3)(C(F)(F)F)C2)c2ccccc12]

Formula (I)

2. Disclosed is an application of the above naphthalene isoxazoline compound, or the chiral monomer or mixture thereof, or the cis-trans isomer monomer or mixture thereof, or the agrichemically acceptable salt, hydrate or solvate thereof in preparation of an insecticide or acaricide.

As one of the preferred technical solutions, the insecticide or acaricide is used for killing pests and/or pest mites in food crops, fiber crops, sugar crops, oil crops, beverage crops, vegetable crops, root and stem crops, fruit crops, dried fruit crops, legume crops, melon crops, flower crops, medicinal crops, industrial raw material crops, or green manure and forage crops.

As one of the preferred technical solutions, the insecticide or acaricide is used for prevention and control of pests and/or pest mites such as lepidoptera (such as diamondback moth, prodenia litura, beet armyworm, cotton bollworm, and fall armyworm), homoptera (such as cotton whiteflies, tobacco whiteflies, and silver leaf whiteflies), thrips (such as *Thrips palmi* Karny, onion thrips, and tobacco thrips), leaf miners, tetranychidae, aphididae or rust mites.

As one of the further preferred technical solutions, the insecticide is used for prevention and control of thrips or aphididae.

As one of the still further preferred technical solutions, the insecticide is used for prevention and control of *Thrips palmi* Karny or *Myzus persicae* Sulzer.

3. Disclosed is a pharmaceutical composition, comprising the above naphthalene isoxazoline compound, or the chiral monomer or mixture thereof, or the cis-trans isomer monomer or mixture thereof, or the agrichemically acceptable salt, hydrate or solvate thereof.

4. Disclosed is an application of the above pharmaceutical composition in preparation of an insecticide or acaricide.

5. Disclosed is an insecticide or acaricide. The effective component of the insecticide or acaricide is the above naphthalene isoxazoline compound, or the chiral monomer or mixture thereof, or the cis-trans isomer monomer or mixture thereof, or the agrichemically acceptable salt, hydrate or solvate thereof.

As one of the preferred technical solutions, during prevention and control of *Thrips palmi* Karny, the effective concentration range of the effective component is 0.012-16 mg/L, further preferably 0.07-10 mg/L, and still further preferably 0.1 mg/L.

As one of the preferred technical solutions, during prevention and control of *Myzus persicae* Sulzer, the effective concentration range of the effective component is 0.4-16 mg/L, further preferably 0.8-10 mg/L, and still further preferably 1.6 mg/L.

As one of the preferred technical solutions, the insecticide or acaricide is prepared into any dosage form by combining the effective component with pesticide formulation auxiliary components allowed in pesticides, including, but not limited to, wettable powder, water dispersible granules, suspending agents, suspension emulsions, aqueous emulsions, micro-emulsions, aqueous agents, missible oil, soluble powder, soluble liquids, granules, microcapsule suspending agents, and microcapsule suspension-suspending agents.

As one of the further preferred technical solutions, the dosage form of the insecticide or acaricide is selected from any one of suspending agents, wettable powder, water dispersible granules, aqueous agents, missible oil or micro-emulsions.

6. Disclosed is an insecticide or acaricide, including the above pharmaceutical composition.

As one of the preferred technical solutions, the insecticide or acaricide is prepared into any dosage form by combining the pharmaceutical composition with pesticide formulation auxiliary components allowed in pesticides, including, but not limited to, wettable powder, water dispersible granules, suspending agents, suspension emulsions, aqueous emulsions, micro-emulsions, aqueous agents, missible oil, soluble powder, soluble liquids, granules, microcapsule suspending agents, and microcapsule suspension-suspending agents.

As one of the further preferred technical solutions, the dosage form of the insecticide or acaricide is selected from any one of suspending agents, wettable powder, water dispersible granules, aqueous agents, missible oil or micro-emulsions.

The disclosure has the following beneficial effects:

The applicant has developed a novel naphthalene-containing oxazolamide pesticide insecticide based on the existing research, which has better insecticidal effects and also has a wider insecticidal range compared with commercially available agricultural insecticides. In addition, a synthesis process for the novel compound is easy to operate and has high safety, and the compound has great application potential.

The novel compound A4 of the disclosure is a novel γ-aminobutyric acid (GABA) gated chloride ion channel allosteric modulator type insecticide, and can be applied to the prevention and control of various pests and/or pest mites in agriculture. Especially, the killing effect of the novel compound A4 on thrips is significantly better than that of the commercially available isoxazole insecticide fluxametamide (compound C4). According to test results, 48 h after administration, the $LC_{50}$ and $LC_{90}$ of the C4 for *Thrips palmi* Karny are 2.6894 mg/L and 16.1203 mg/L respectively, and the $LC_{50}$ and $LC_{90}$ of the A4 for *Thrips palmi* Karny are 0.0123 mg/L and 0.0705 mg/L respectively. As a result, the $LC_{90}$ value of the A4 for *Thrips palmi* Karny is only 4/1000 of the $LC_{90}$ value of the C4 for *Thrips palmi* Karny, so the A4 has significantly higher toxicity to *Thrips palmi* Karny.

The novel compound A4 of the disclosure can effectively prevent and control pests and/or pest mites such as thrips, whiteflies, leaf miners, beetles, red spider mites and rust mites, and can also effectively prevent and control pests such as aphids and butterfly moths. Especially, the killing effect of the novel compound A4 on aphids is significantly better than that of fluxametamide. According to test results, 48 h after administration, the $LC_{50}$ of the C4 and A4 for aphids is 1.1007 mg/L and 0.4390 mg/L respectively. As a result, the $LC_{50}$ value of the A4 for *Myzus persicae* Sulzer is only 40/100 of the $LC_{50}$ value of the C4 for *Myzus persicae* Sulzer, so the A4 has significantly higher toxicity to *Myzus persicae* Sulzer.

Compared with a compound B4 (4-(5-(3,5-dichlorophenyl)-5-(trifluoromethyl)-4,5-dihydroisoxazol-3-yl)-N-((methoxylimino)methyl)-1-naphthyl formamide) having a similar structure, the novel compound A4 of the disclosure has a superior killing effect on common agricultural pests such as thrips and aphids. The chemical structural formula of the compound B4 is as follows:

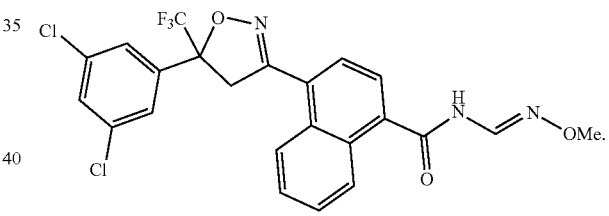

Test results show that 48 h after administration, the $LC_{50}$ and $LC_{90}$ of the B4 for *Thrips palmi* Karny are 3.3311 mg/L and 33.9739 mg/L respectively, and the $LC_{50}$ and $LC_{90}$ of the A4 for *Thrips palmi* Karny are 0.0123 mg/L and 0.0705 mg/L respectively. As a result, the $LC_{90}$ value of the A4 for *Thrips palmi* Karny is 2/1000 of the $LC_{90}$ value of the B4 for *Thrips palmi* Karny, so the A4 has significantly higher toxicity to *Thrips palmi* Karny.

48 h after administration, the $LC_{50}$ of the B4 and A4 for aphids is 3.1342 mg/L and 0.4390 mg/L respectively. As a result, the $LC_{50}$ value of the A4 for *Myzus persicae* Sulzer is 14/100 of the $LC_{50}$ value of the B4 for *Myzus persicae* Sulzer, so the A4 has significantly higher toxicity to *Myzus persicae* Sulzer.

Therefore, the novel compound A4 of the disclosure can be used for killing various pests and/or pest mites in agricultural production, and has great application and promotion value.

DETAILED DESCRIPTION OF THE EMBODIMENTS

The disclosure will be further explained below with reference to accompanying drawings and embodiments. It should be noted that the following description is only for the purpose of explaining the disclosure and does not limit the content thereof.

Embodiment 1

Figure 1:
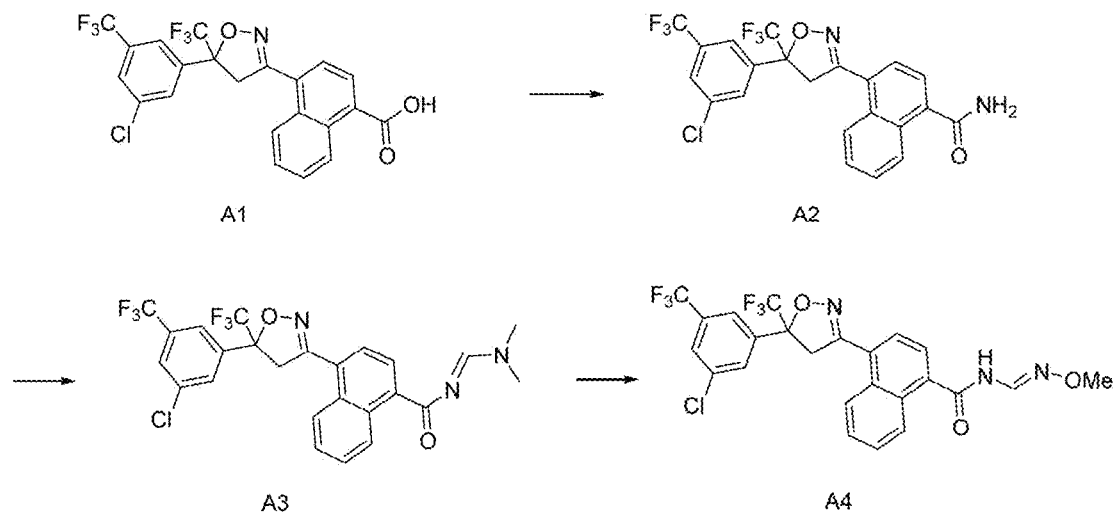
FIG. 1 shows a synthesis route of a compound A4.

FIG. 1 shows a synthesis route of a compound A4. Specific steps were as follows:
(1) Synthesis of Compound A2

At a room temperature (25° C.), a compound A1 (10 g, 20.5 mmol) was taken and dissolved in dichloromethane (80 ml), where A1 was 4-(5-(3-chloro-5-(trifluoromethyl)phenyl)-5-(trifluoromethyl)-4,5-dihydroisoxazol-3-yl)-1-naphthoic acid purchased from Dezhou Hanhua Pharmaceutical Chemistry Co., Ltd. The solution was stirred, thionyl chloride (4.87 g, 40.93 mmol) was added, and the temperature was raised for refluxing (40° C.). Heat preservation was performed for refluxing for 3.5 h to complete the reaction, concentration was performed under reduced pressure, tetrahydrofuran (50 mL) was added and dissolved, and aqueous ammonia (mass fraction: 25%, 20 ml) was added dropwise in an ice-water bath. The reaction was basically completed after reacting at a room temperature for 0.5 h. Concentration was performed under reduced pressure, ethyl acetate (80 ml) and water (60 ml) were added, the solution was separated, organic phases were washed with water once, aqueous phases were mixed, ethyl acetate was extracted once, organic phases were mixed, drying was performed with anhydrous sodium sulfate, and concentration was performed under reduced pressure to obtain 12.18 g of light yellow solids.

Ethyl acetate/n-hexane recrystallization: 12.18 g of the obtained light yellow solids were dissolved in 24.36 g of ethyl acetate and heated for refluxing. The temperature of the solution was reduced to a room temperature, 48.72 g of n-hexane was slowly added dropwise, and the solution was allowed to stand for precipitating solids. The solids were filtered out and blown at 40° C. overnight to obtain 8.86 g of white solids (compound A2) with a yield of 88.9%.
(2) Synthesis of Compound A3

At a room temperature, the compound A2 (5 g) was taken and added to N,N-dimethylformamide dimethylacetal (95 g), nitrogen replacement was performed, the system was light yellow and turbid, the system was dissolved and becomes clear during temperature rise, the heat preservation reaction was performed at 70° C. for 1 h to complete the reaction, concentration was performed under reduced pressure to obtain 6.4 g of a brown oily matter, 100 mL of ethyl acetate alkalized with triethylamine (triethylamine and ethyl acetate were mixed in a volume ratio of 1:1000) was added and dissolved, 10 g of activated carbon was added, the solution was stirred for 0.5 h and then filtered, and the filtrate was concentrated under reduced pressure to obtain 5.94 g of a yellow oily matter (compound A3).
(3) Synthesis of Compound A4

At a room temperature, the compound A3 (5.94 g, 10.96 mmol) was taken and dissolved in 1,4-dioxane (90 ml), the solution was stirred, the system was yellow and clear, a methoxyamine hydrochloride aqueous solution (obtained by dissolving 1.59 g of methoxyamine hydrochloride in 17.8 g of water) was added, the reaction was performed at 25° C. for 3.5 h to complete the reaction, concentration was performed under reduced pressure, ethyl acetate (60 ml) was added and dissolved, the solution was washed with water (30 ml) and saturated salt solution (30 ml) in sequence, drying was performed with anhydrous sodium sulfate, concentration was performed under reduced pressure to obtain 5.78 g of a yellow oily matter, and column chromatography (petroleum ether (PE):ethyl acetate (EA)=3:1, volume ratio) was performed for purification to obtain 4.86 g of white solids (compound A4) with a yield of 81.5%.

$^1$H NMR (400 MHZ, CDCl$_3$), δ (ppm): 8.84 (d, J=8, 1H), 8.65 (d, J=8, 1H), 8.34 (d, J=8, 1H), 7.84 (d, J=24, 3H), 7.68-7.73 (m, 4H), 7.56 (d, J=8, 1H), 4.32 (d, J=16, 1H), 3.93 (d, J=20, 1H), 3.89 (s, 3H). C$_{24}$H$_{16}$ClF$_6$N$_3$O$_3$ [M+H$^+$] =544.10.

Comparative Example 1

Figure 2:
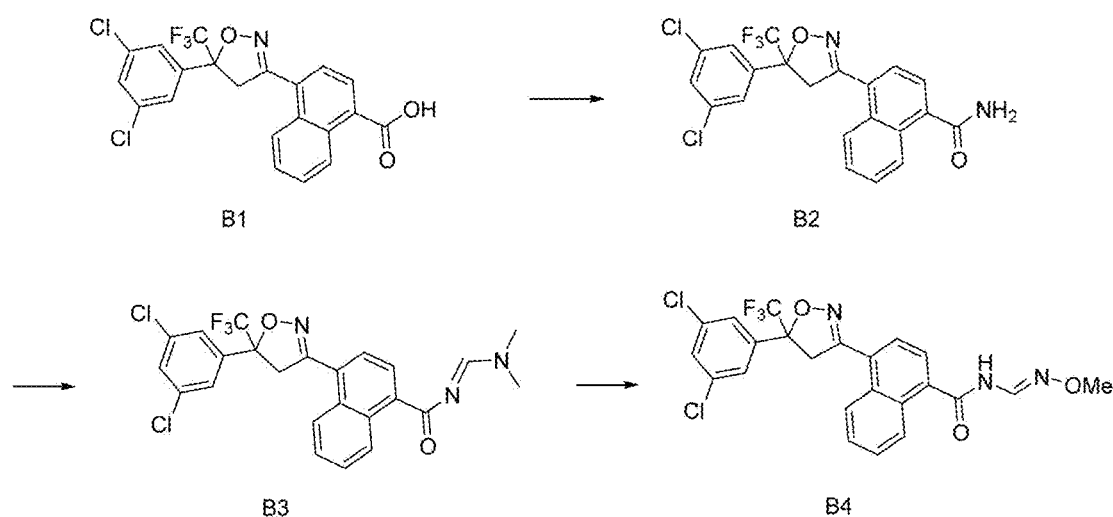
FIG. 2 shows a synthesis route of a compound B4.

FIG. 2 shows a synthesis route of a compound B4. Specific steps were as follows:
(1) Synthesis of Compound B2

At a room temperature (20° C.), a compound B1 (7 g, 15.41 mmol) was taken and dissolved in dichloromethane (56 ml), where B1 was 4-(5-(3,5-dichlorophenyl)-5-(trifluoromethyl)-4,5-dihydroisoxazol-3-yl)-1-naphthoic acid (purchased from Dezhou Hanhua Pharmaceutical Chemistry Co., Ltd.). The solution was stirred, thionyl chloride (3.66 g, 19.37 mmol) was added, the temperature was raised for refluxing (40° C.), the reaction was performed at 40° C. for 5.5 h, then concentration was performed under reduced pressure, tetrahydrofuran (35 mL) was added and dissolved, aqueous ammonia (commercially available, mass concentration: 25%, 14 ml) was added dropwise in an ice-water bath, and the reaction was completed after 0.5 h. Concentration was performed under reduced pressure, ethyl acetate (80 ml) and water (60 ml) were added, the solution was separated, organic phases were washed with water once, aqueous phases were mixed, ethyl acetate was extracted once, organic phases were mixed, drying was performed with anhydrous sodium sulfate, and concentration was performed under reduced pressure to obtain 18.32 g of a yellow sticky matter. 100 ml of ethyl acetate was added and dissolved, then 400 ml of n-hexane was added, and a large number of white solids were precipitated, filtered and blown at 40° C. overnight to obtain 4.77 g of white solids (compound B2) with a yield of 68.3%.
(2) Synthesis of Compound B3

At a room temperature (20° C.), the compound B2 (4.77 g, 10.52 mmol) was taken and added to 90 g of N,N-dimethylformamide dimethylacetal, nitrogen replacement was performed, the system was light yellow and turbid, the system was dissolved and becomes clear during temperature rise, the heat preservation reaction was performed at 70° C. for 1.5 h to complete the reaction, concentration was performed under reduced pressure to obtain 6.72 g of a brown oily matter, 100 mL of ethyl acetate alkalized with triethylamine (triethylamine and ethyl acetate were mixed in a volume ratio of 1:1000) was added and dissolved, 10 g of activated carbon was added, the solution was stirred for 0.5 h and then filtered, and the filtrate was concentrated under reduced pressure to obtain 5.76 g of a yellow oily matter (compound B3) with a yield of 97.7%.
(3) Synthesis of Compound B4

At a room temperature (20° C.), the compound B3 (5.76 g, 11.33 mmol) was taken and dissolved in 1,4-dioxane (86 ml), the solution was stirred, the system was yellow and clear, a methoxyamine hydrochloride aqueous solution (obtained by dissolving 1.66 g of methoxyamine hydrochloride in 17 g of water) was added, the reaction was performed at 25° C. for 2 h to complete the reaction, concentration was performed under reduced pressure to obtain 9.32 g of a yellow oily matter, ethyl acetate (60 ml) was added and dissolved, the solution was washed with water (30 ml) and saturated salt solution (30 ml) in sequence, drying was performed with anhydrous sodium sulfate, and concentration was performed under reduced pressure to obtain 4.76 g of white solids (compound B4) with a yield of 82.3%.

$^1$H NMR (400 MHZ, DMSO-d6), δ (ppm): 11.13 (s, 1H), 8.81 (d, J=8, 1H), 8.13 (d, J=8, 1H), 7.92 (d, J=8, 1H), 7.70-7.85 (m, 7H), 4.56 (s, 2H), 3.79 (s, 3H). $C_{23}H_{16}Cl_2F_3N_3O_3$ [M+H$^+$]=510.04.

Comparative Example 2

Figure 3:
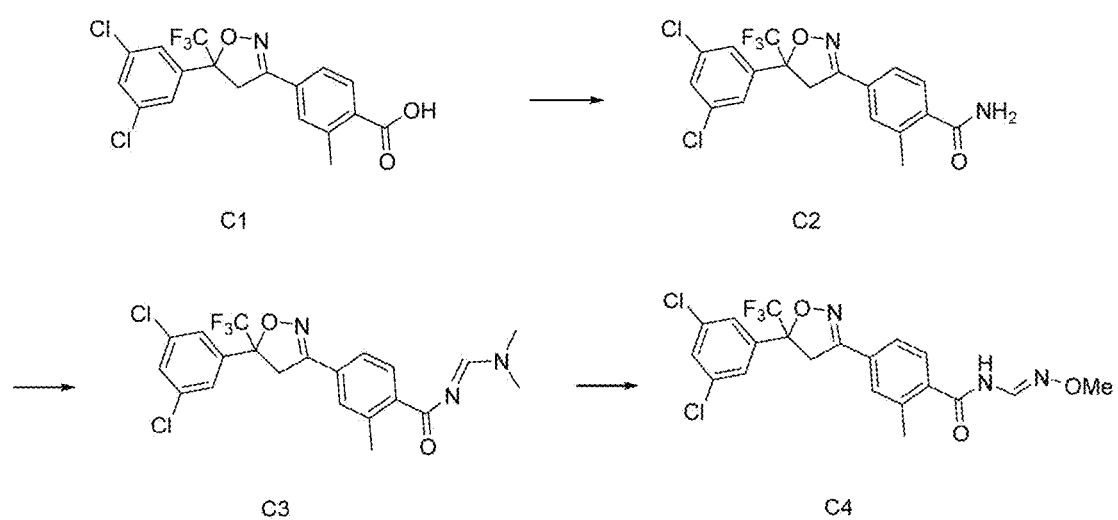
FIG. 3 shows a synthesis route of a compound C4.

FIG. 3 shows a synthesis route of a compound C4. Specific steps were as follows:
(1) Synthesis of Compound C2

At a room temperature (25° C.), a compound C1 (12 g, 28.7 mmol) was taken and dissolved in dichloromethane (96 ml), where C1 was 4-(5-(3-chloro-5-methyl-4,5-dihydroisoxazol-3-yl)-2-methyl-benzoic acid (purchased from Dezhou Hanhua Pharmaceutical Chemistry Co., Ltd.). The solution was stirred, thionyl chloride (6.83 g, 57.4 mmol) was added, and the temperature was raised for refluxing. The reaction was completed after 3 h, concentration was performed under reduced pressure, tetrahydrofuran (60 ml) was added and dissolved, and aqueous ammonia (mass concentration: 25%, 24 g) was added dropwise in an ice-water bath. The reaction was basically completed after reacting at a room temperature for 0.5 h. Concentration was performed under reduced pressure, ethyl acetate (96 ml) and water (72 ml) were added, the solution was separated, organic phases were washed with water once, aqueous phases were mixed, ethyl acetate was extracted once, organic phases were mixed, drying was performed with anhydrous sodium sulfate, and concentration was performed under reduced pressure to obtain 15 g of light yellow solids.

Ethyl acetate/n-hexane recrystallization: 15 g of the obtained light yellow solids were dissolved in 30 g of ethyl acetate and heated for refluxing. The temperature of the solution was reduced to a room temperature, 60 g of n-hexane was slowly added dropwise, and the solution was allowed to stand for precipitating solids. The solids were filtered out and blown at 40° C. overnight to obtain 10.87 g of white solids (compound C2) with a yield of 90.8%.
(2) Synthesis of Compound C3

At a room temperature, 5.5 g of the compound C2 was taken and added to 104 g of N,N-dimethylformamide dimethylacetal, nitrogen replacement was performed, the system was light yellow and turbid, the system was dissolved and becomes clear during temperature rise, the heat preservation reaction was performed at 70° C. for 0.5 h to complete the reaction, concentration was performed under reduced pressure to obtain 7 g of a brown oily matter, 100 mL of ethyl acetate alkalized with triethylamine (triethylamine and ethyl acetate were mixed in a volume ratio of 1:1000) was added and dissolved, 10 g of activated carbon was added, the solution was stirred for 0.5 h and then filtered, and the filtrate was concentrated under reduced pressure to obtain 6.4 g of a yellow oily matter (compound C3).
(3) Synthesis of Compound C4

At a room temperature, the compound C3 (6.4 g, 13.55 mmol) was taken and dissolved in 96 ml of 1,4-dioxane, the solution was stirred, the system was yellow and clear, a methoxyamine hydrochloride aqueous solution (obtained by dissolving 1.97 g of methoxyamine hydrochloride in 22 g of water) was added, the reaction was performed at 25° C. for 2 h to complete the reaction, concentration was performed under reduced pressure, ethyl acetate (64 ml) was added and dissolved, the solution was washed with water (32 ml) and saturated salt solution (32 ml) in sequence, drying was performed with anhydrous sodium sulfate, concentration was performed under reduced pressure to obtain 6.12 g of a yellow oily matter, and column chromatography (petroleum ether (PE):ethyl acetate (EA)=3:1, volume ratio) was performed for purification to obtain 5.49 g of white solids (compound C4) with a yield of 85.5%.

$^1$H NMR (400 MHZ, CDCl$_3$), δ (ppm): 8.49 (d, J=8, 1H), 7.77 (d, J=8, 1H), 7.43-7.60 (m, 6H), 4.09 (d, J=16, 1H), 3.90 (s, 3H), 3.71 (d, J=20, 1H), 2.53 (s, 3H). $C_{20}H_{16}Cl_2F_3N_3O_3$ [M+H$^+$]=474.05.

Test Example

Pest prevention and control tests were performed on the compound A4, compound B4 and compound C4 obtained in Embodiment 1 and Comparative Examples 1 and 2 respectively. A specific method was as follows:
I. *Thrips palmi* Karny Prevention and Control Test
1. Test Purpose:

Through indoor tests, a liquid tube drug film method improved by a filter paper drug film method was used for evaluating the indoor toxicity effects of three raw drugs on *Thrips palmi* Karny.
2. Test Conditions:
2.1 Preparation of Test Material

*Thrips palmi* Karny was raised indoors in the insectary of the Plant Protection Institute of Shandong Academy of Agricultural Sciences.
2.2 Culture Conditions Culture was performed in an illumination incubator, and raising and observation were performed under the conditions that the temperature was 25.0±2.0° C., the relative humidity was 75±5% and the photoperiod (L/D) was 14 h/10 h.
2.3 Instruments and Equipment Illumination incubator, micro-sampler, volumetric flask, electronic balance, beaker, sealing film, centrifugal tube (1.5 mL), filter paper, needle, tweezers, marker pen, writing brush, and glass rod.
3. Test Design:
3.1 Reagent
3.1.1 Test Medicaments and Insect for Tests Three compounds B4, C4 and A4 were used as test medicaments.

The insect for tests is an adult of *Thrips palmi* Karny.
3.1.2 Solvent for Tests
Methanol
3.2 Test Processing
3.2.1 Dose Setting Three test medicaments were prepared into a mother solution with methanol and then diluted with a Tween-80 aqueous solution having a mass concentration of 0.1% in equal proportions, and the concentration was set in equal proportions.

B4 concentration: 0.5, 1, 2, 4, 8, 16 mg/L;
C4 concentration: 25, 12.5, 6.25, 3.125, 1.5625, 0.7813 mg/L;
A4 concentration: 0.1, 0.05, 0.025, 0.0125, 0.00625, 0.003125 mg/L.
3.2.2 Test Repetition Each processing was repeated 4 times, and 30 insects for tests were used for each repetition.

4. Test Method:

According to NY/T 1154.8-2007, the liquid tube drug film method improved by the filter paper drug film method was used for processing insects for tests. Medicaments for tests were diluted into 6 concentrations, a 1.5 mL centrifugal tube was filled with each concentration of liquid medicine respectively and allowed to stand for 4 h, then the liquid medicine was poured out, and the centrifugal tube was placed on a test table and air-dried for later use. A fine needle tip was heated with an alcohol lamp, and a small hole with a diameter of about 2-3 mm was formed at the bottom of the air-dried centrifugal tube by heating. One repetition was performed for each tube, and 4 repetitions were performed for each concentration. Leaf soaking: A hole puncher was used for punching fresh cabbage leaves into circular leaves with a diameter of 0.5 cm, and the circular leaves were respectively soaked in each concentration of liquid medicine for 10 s with leaf soaking in clear water as a control. The processed leaves were placed on absorbent paper and air-dried and then clamped with small tweezers into the centrifugal tubes with corresponding liquid medicine concentrations, and one leaf was placed flatly in each tube. Indoor insects for tests: An interface of an insect sucker was sealed with gauze and sleeves an orifice of the processed centrifugal tube, and the hole formed by heating at the bottom of the centrifugal tube was aligned with the insects for tests to enable the insects for tests to be sucked into the centrifugal tube along the airflow. The insects for tests were processed after control, about 30 insects for tests were sucked for each repetition, then a tube cover was covered, and the hole formed by heating was sealed with a sealing film. After related information was marked, the number of live insects and the number of dead insects were recorded 48 h later.

5. Data Investigation and Statistic Analysis:

5.1 Investigation Method and Grading Standard

The insects were lightly touched with a writing brush, and the insects that do not respond were considered dead.

5.2 Investigation Time

Test results were investigated 48 h after drug post-processing.

5.3 Computing Method $$\text{Death rate}(100\%) = \frac{\text{Number of dead insects}}{\text{Total number of processed insects}} \times 100$$

$$\text{Corrected death rate}(100\%) = \frac{\text{Processed death rate} - \text{Blank control death rate}}{100 - \text{Blank control death rate}} \times 100$$

The logarithm of the medicament concentration (mg/L) was taken as an independent variable X, the probability value of a corrected death rate was taken as a dependent variable Y, and the $LC_{50}$ value, $LC_{90}$ value, 95% confidence limit and $R^2$ of a toxicity regression line were computed by DPS software.

5.4 Data Statistic Analysis

TABLE 1-1

Indoor toxicity test data table of test medicament B4 for *Thrips palmi* Karny (48 h)

| Medicament concentration (mg/L) | Repetition | Number of insects for tests (head) | Number of dead insects (head) | Death rate (%) |
|---|---|---|---|---|
| 0 | 1 | 27 | 2 | 7.41 |
|  | 2 | 19 | 0 | 0.00 |
|  | 3 | 28 | 1 | 3.57 |
|  | 4 | 15 | 0 | 0.00 |
|  | Total/Average | 89 | 3 | 2.74 |

TABLE 1-1-continued

Indoor toxicity test data table of test medicament B4 for *Thrips palmi* Karny (48 h)

| Medicament concentration (mg/L) | Repetition | Number of insects for tests (head) | Number of dead insects (head) | Death rate (%) |
|---|---|---|---|---|
| 0.5 | 1 | 20 | 4 | 20.00 |
|  | 2 | 13 | 3 | 23.08 |
|  | 3 | 21 | 4 | 19.05 |
|  | 4 | 18 | 2 | 11.11 |
|  | Total/Average | 72 | 13 | 18.31 |
| 1 | 1 | 18 | 4 | 22.22 |
|  | 2 | 14 | 2 | 14.29 |
|  | 3 | 14 | 9 | 64.29 |
|  | 4 | 15 | 3 | 20.00 |
|  | Total | 61 | 18 | 30.20 |
| 2 | 1 | 26 | 8 | 30.77 |
|  | 2 | 19 | 7 | 36.84 |
|  | 3 | 18 | 5 | 27.78 |
|  | 4 | 25 | 10 | 40.00 |
|  | Total/Average | 88 | 30 | 33.85 |
| 4 | 1 | 25 | 13 | 52.00 |
|  | 2 | 29 | 12 | 41.38 |
|  | 3 | 33 | 18 | 54.55 |
|  | 4 | 26 | 11 | 42.31 |
|  | Total/Average | 113 | 54 | 47.56 |
| 8 | 1 | 24 | 19 | 79.17 |
|  | 2 | 25 | 17 | 68.00 |
|  | 3 | 24 | 14 | 58.33 |
|  | 4 | 24 | 15 | 62.50 |
|  | Total/Average | 97 | 65 | 67.00 |
| 16 | 1 | 21 | 21 | 100.00 |
|  | 2 | 19 | 18 | 94.74 |
|  | 3 | 24 | 24 | 100.00 |
|  | 4 | 25 | 25 | 100.00 |
|  | Total/Average | 89 | 88 | 98.68 |

TABLE 1-2

Indoor toxicity test data table of test medicament C4 for *Thrips palmi* Karny (48 h)

| Medicament concentration (mg/L) | Repetition | Number of insects for tests (head) | Number of dead insects (head) | Death rate (%) |
|---|---|---|---|---|
| 0 | 1 | 21 | 1 | 4.76 |
|  | 2 | 18 | 1 | 5.56 |
|  | 3 | 16 | 0 | 0.00 |
|  | 4 | 22 | 1 | 3.44 |
|  | Total/Average | 77 | 3 | 3.44 |
| 0.7813 | 1 | 20 | 2 | 10.00 |
|  | 2 | 18 | 2 | 11.11 |
|  | 3 | 20 | 5 | 25.00 |
|  | 4 | 17 | 2 | 11.76 |
|  | Total/Average | 75 | 11 | 14.47 |
| 1.5625 | 1 | 20 | 6 | 30.00 |
|  | 2 | 14 | 3 | 21.43 |
|  | 3 | 18 | 6 | 33.33 |
|  | 4 | 19 | 3 | 15.79 |
|  | Total/Average | 71 | 18 | 25.14 |

TABLE 1-2-continued

Indoor toxicity test data table of test medicament C4 for *Thrips palmi* Karny (48 h)

| Medicament concentration (mg/L) | Repetition | Number of insects for tests (head) | Number of dead insects (head) | Death rate (%) |
|---|---|---|---|---|
| 3.125 | 1 | 17 | 12 | 70.59 |
|  | 2 | 19 | 12 | 63.16 |
|  | 3 | 20 | 14 | 70.00 |
|  | 4 | 23 | 14 | 60.87 |
|  | Total/Average | 79 | 52 | 66.15 |
| 6.25 | 1 | 28 | 24 | 85.71 |
|  | 2 | 25 | 22 | 88.00 |
|  | 3 | 24 | 18 | 75.00 |
|  | 4 | 29 | 23 | 79.31 |
|  | Total/Average | 106 | 87 | 82.01 |
| 12.5 | 1 | 27 | 24 | 88.89 |
|  | 2 | 27 | 23 | 85.19 |
|  | 3 | 16 | 14 | 87.50 |
|  | 4 | 20 | 18 | 90.00 |
|  | Total/Average | 90 | 79 | 87.89 |
| 25 | 1 | 24 | 23 | 95.83 |
|  | 2 | 23 | 22 | 95.65 |
|  | 3 | 20 | 20 | 100.00 |
|  | 4 | 23 | 22 | 95.65 |
|  | Total/Average | 90 | 87 | 96.78 |

TABLE 1-3

Indoor toxicity test data table of test medicament A4 for *Thrips palmi* Karny (48 h)

| Medicament concentration (mg/L) | Repetition | Number of insects for tests (head) | Number of dead insects (head) | Death rate (%) |
|---|---|---|---|---|
| 0 | 1 | 24 | 0 | 0.00 |
|  | 2 | 20 | 0 | 0.00 |
|  | 3 | 24 | 1 | 4.17 |
|  | 4 | 17 | 1 | 5.88 |
|  | Total/Average | 85 | 2 | 2.51 |
| 0.003125 | 1 | 20 | 4 | 20.00 |
|  | 2 | 21 | 0 | 0.00 |
|  | 3 | 16 | 1 | 6.25 |
|  | 4 | 22 | 3 | 13.64 |
|  | Total/Average | 79 | 8 | 9.97 |
| 0.00625 | 1 | 20 | 7 | 35.00 |
|  | 2 | 17 | 5 | 29.41 |
|  | 3 | 19 | 8 | 42.11 |
|  | 4 | 18 | 8 | 44.44 |
|  | Total/Average | 74 | 28 | 37.74 |
| 0.0125 | 1 | 20 | 11 | 55.00 |
|  | 2 | 20 | 12 | 60.00 |
|  | 3 | 23 | 16 | 69.57 |
|  | 4 | 20 | 12 | 60.00 |
|  | Total/Average | 83 | 51 | 61.14 |
| 0.025 | 1 | 27 | 23 | 85.19 |
|  | 2 | 23 | 17 | 73.91 |
|  | 3 | 21 | 17 | 80.95 |
|  | 4 | 22 | 18 | 81.82 |
|  | Total/Average | 93 | 75 | 80.47 |
| 0.05 | 1 | 21 | 18 | 85.71 |
|  | 2 | 23 | 21 | 91.30 |
|  | 3 | 18 | 17 | 94.44 |
|  | 4 | 27 | 25 | 92.59 |
|  | Total/Average | 89 | 81 | 91.01 |
| 0.1 | 1 | 21 | 21 | 100.00 |
|  | 2 | 20 | 20 | 100.00 |
|  | 3 | 27 | 27 | 100.00 |
|  | 4 | 24 | 24 | 100.00 |
|  | Total/Average | 92 | 92 | 100.00 |

TABLE 2

Indoor toxicity test results of three test medicaments for *Thrips palmi* Karny (48 h)

| Medicament name | Regression equation | $R^2$ | $LC_{50}$ (mg/L) | 95% confidence limit (mg/L) | $LC_{90}$ (mg/L) | 95% confidence limit (mg/L) |
|---|---|---|---|---|---|---|
| B4 | Y = 4.1477 + 1.6309X | 0.9033 | 3.3311 | 2.1616-5.5203 | 33.9739 | 14.9232-233.4734 |
| C4 | Y = 4.0934 + 2.0614X | 0.9838 | 2.6894 | 2.1187-3.172 | 16.1203 | 12.828-21.5341 |
| A4 | Y = 9.3648 + 2.1975X | 0.9924 | 0.0123 | 0.0102-0.0139 | 0.0705 | 0.0705-0.1318 |

6. Result Analysis

Test results (see Table 1-1-1-3 and Table 2) show that 48 h after administration, the $LC_{50}$ and $LC_{90}$ of the B4 for *Thrips palmi* Karny were 3.3311 mg/L and 33.9739 mg/L respectively, the $LC_{50}$ and $LC_{50}$ of the C4 for *Thrips palmi* Karny were 2.6894 mg/L and 16.1203 mg/L respectively, and the $LC_{50}$ and $LC_{90}$ of the A4 for *Thrips palmi* Karny were 0.0123 mg/L and 0.0705 mg/L respectively.

Conclusion: The $LC_{90}$ value of the A4 for *Thrips palmi* Karny was only 4/1000 of the $LC_{90}$ value of the C4 for *Thrips palmi* Karny, and was 2/1000 of the $LC_{90}$ value of the B4 for *Thrips palmi* Karny, so the A4 has the highest toxicity to *Thrips palmi* Karny.

II. *Myzus persicae* Sulzer Prevention and Control Test

1. Material and Method 1.1 Organism for Tests, Source and Test Material Number

The aphid species was *Myzus persicae* Sulzer, which was a sensitive population raised indoors in the bioassay room of the Plant Protection Institute of Shandong Academy of Agricultural Sciences. The temperature range was 24-26° C., the humidity range was 60%-80%, and the illumination was L:D=16 h:8 h. Aphids used for tests were wingless aphids.

1.2 Main Instruments and Equipment

One ten-thousandth electronic balance (Shimadzu Corporation, model: ATX224), pipette (Eppendorf, Germany), artificial climate chamber (Jiangnan Instrument Factory, Ningbo, model: RXZ-280C), beaker, volumetric flask, measuring cylinder, disposable plastic cup (bottom diameter 6 cm×mouth diameter 9 cm×height 7 cm), etc.

1.3 Test Method 1.3.1 Test Concentration and Proportion Setting

Test medicaments were prepared into a mother solution with methanol and then diluted with a Tween-80 aqueous solution having a mass concentration of 0.1% in equal proportions. According to effective components, the B4 was set to 6 concentration gradients of 0.5 mg/L, 1 mg/L, 2 mg/L, 4 mg/L, 8 mg/L, and 16 mg/L; the C4 was set to 6 concentration gradients of 0.5 mg/L, 1 mg/L, 2 mg/L, 4 mg/L, 8 mg/L, and 16 mg/L; and the A4 was set to 6 concentration gradients of 0.05 mg/L, 0.1 mg/L, 0.2 mg/L, 0.4 mg/L, 0.8 mg/L, and 1.6 mg/L. A methanol aqueous solution having a volume concentration of 4% was taken as a blank control.

1.3.2 Contamination

Insects for tests were processed according to an insect soaking method (NY/T 1154.6-2006) and a leaf soaking method (NY/T 1154.14-2008). Each medicament for tests was diluted to the set 6 concentrations for later use. Absorbent paper was placed at the bottom of a disposable plastic cup, a layer of filter paper was laid on the absorbent paper, and 2 mL of distilled water was added to keep moisture for later use. Leaves with aphids were cut into small leaves, each leaf has about 20 wingless aphids, and the leaves with aphids were gently soaked in the liquid medicine with tweezers and then taken out after 10 s, and placed on the absorbent paper and air-dried. The air-dried leaves were placed in the prepared plastic cups which were then covered, and one leaf was placed in each plastic cup. One repetition was performed for each plastic cup, and 4 repetitions were performed for each concentration. The plastic cups were placed in an illumination incubator, and the number of live aphids and the number of dead aphids were recorded 48 h later.

1.4 Data Processing

DPS software was used for processing, and the median lethal concentration $LC_{50}$ and 95% confidence limit of 3 test medicaments on aphids at 48 h were determined.

1.5 Quality Control

Quality control conditions include:
(1) The death rate of the control group does not exceed 10%.
(2) The temperature range was 24-26° C., the humidity range was 60-80%, and the illumination was L:D=16 h:8 h.

1.6 Computing Method $$\text{Death rate}(100\%) = \frac{\text{Number of dead insects}}{\text{Total number of processed insects}} \times 100$$

$$\text{Corrected death rate}(100\%) = \frac{\text{Processed death rate} - \text{Blank control death rate}}{100 - \text{Blank control death rate}} \times 100$$

The logarithm of the medicament concentration (mg/L) was taken as an independent variable X, the probability value of a corrected death rate was taken as a dependent variable Y, and the $LC_{50}$ value, 95% confidence limit and R2 of a toxicity regression line were computed by DPS software.

2. Results and Conclusion 2.1 Actual Measurement Data for Quality Control (1) After tests, the death rate of the blank control group was less than 10%.
(2) During tests, the temperature was 24.6-25.5° C., and the relative humidity was 70-78%.

2.2 Results

TABLE 3-1

Indoor toxicity test data table of test medicament B4 for *Myzus persicae* Sulzer (48 h)

| Medicament concentration (mg/L) | Repetition | Number of insects for tests (head) | Number of dead insects (head) | Death rate (%) |
|---|---|---|---|---|
| 16 | 1 | 22 | 18 | 81.82 |
|  | 2 | 26 | 21 | 80.77 |
|  | 3 | 27 | 24 | 88.89 |
|  | 4 | 23 | 20 | 86.96 |
|  | Total | 98 | 83 | 84.61 |
| 8 | 1 | 21 | 17 | 80.95 |
|  | 2 | 24 | 16 | 66.67 |
|  | 3 | 28 | 24 | 85.71 |
|  | 4 | 25 | 20 | 80.00 |
|  | Total | 98 | 77 | 78.33 |
| 4 | 1 | 31 | 13 | 41.94 |
|  | 2 | 24 | 14 | 58.33 |
|  | 3 | 25 | 18 | 72.00 |
|  | 4 | 29 | 21 | 72.41 |
|  | Total | 109 | 66 | 61.17 |
| 2 | 1 | 38 | 9 | 23.68 |
|  | 2 | 33 | 19 | 57.58 |
|  | 3 | 34 | 16 | 47.06 |
|  | 4 | 25 | 13 | 52.00 |
|  | Total | 130 | 57 | 45.08 |
| 1 | 1 | 33 | 5 | 15.15 |
|  | 2 | 18 | 4 | 22.22 |
|  | 3 | 23 | 5 | 21.74 |
|  | 4 | 21 | 5 | 23.81 |
|  | Total | 95 | 19 | 20.73 |

TABLE 3-1-continued

Indoor toxicity test data table of test medicament B4 for *Myzus persicae* Sulzer (48 h)

| Medicament concentration (mg/L) | Repetition | Number of insects for tests (head) | Number of dead insects (head) | Death rate (%) |
|---|---|---|---|---|
| 0.5 | 1 | 20 | 2 | 10.00 |
|  | 2 | 32 | 4 | 12.50 |
|  | 3 | 24 | 3 | 12.50 |
|  | 4 | 23 | 3 | 13.04 |
|  | Total | 99 | 12 | 12.01 |
| 0 | 1 | 27 | 0 | 0.00 |
|  | 2 | 30 | 2 | 6.67 |
|  | 3 | 32 | 3 | 9.38 |
|  | 4 | 25 | 0 | 0.00 |
|  | Total | 114 | 5 | 4.01 |

TABLE 3-2

Indoor toxicity test data table of test medicament C4 for *Myzus persicae* Sulzer (48 h)

| Medicament concentration (mg/L) | Repetition | Number of insects for tests (head) | Number of dead insects (head) | Death rate (%) |
|---|---|---|---|---|
| 16 | 1 | 22 | 21 | 95.45 |
|  | 2 | 26 | 26 | 100.00 |
|  | 3 | 30 | 28 | 93.33 |
|  | 4 | 29 | 29 | 100.00 |
|  | Total | 107 | 104 | 97.20 |
| 8 | 1 | 24 | 22 | 91.67 |
|  | 2 | 27 | 25 | 92.59 |
|  | 3 | 26 | 26 | 100.00 |
|  | 4 | 27 | 27 | 100.00 |
|  | Total | 104 | 100 | 96.06 |
| 4 | 1 | 28 | 25 | 89.29 |
|  | 2 | 25 | 22 | 88.00 |
|  | 3 | 31 | 27 | 87.10 |
|  | 4 | 27 | 21 | 77.78 |
|  | Total | 111 | 95 | 85.54 |
| 2 | 1 | 28 | 24 | 85.71 |
|  | 2 | 27 | 21 | 77.78 |
|  | 3 | 28 | 21 | 75.00 |
|  | 4 | 21 | 15 | 71.43 |
|  | Total | 104 | 81 | 77.48 |
| 1 | 1 | 23 | 11 | 47.83 |
|  | 2 | 22 | 8 | 36.36 |
|  | 3 | 25 | 10 | 40.00 |
|  | 4 | 30 | 18 | 60.00 |
|  | Total | 100 | 47 | 46.05 |
| 0.5 | 1 | 20 | 5 | 25.00 |
|  | 2 | 35 | 9 | 25.71 |
|  | 3 | 24 | 4 | 16.67 |
|  | 4 | 27 | 5 | 18.52 |
|  | Total | 106 | 23 | 21.47 |
| 0 | 1 | 17 | 0 | 0.00 |
|  | 2 | 18 | 0 | 0.00 |
|  | 3 | 23 | 1 | 4.35 |
|  | 4 | 31 | 0 | 0.00 |
|  | Total | 89 | 1 | 1.09 |

TABLE 3-3

Indoor toxicity test data table of test medicament A4 for *Myzus persicae* Sulzer (48 h)

| Medicament concentration (mg/L) | Repetition | Number of insects for tests (head) | Number of dead insects (head) | Death rate (%) |
|---|---|---|---|---|
| 1.6 | 1 | 29 | 25 | 86.21 |
|  | 2 | 30 | 25 | 83.33 |
|  | 3 | 31 | 27 | 87.10 |
|  | 4 | 32 | 26 | 81.25 |
|  | Total | 122 | 103 | 84.47 |
| 0.8 | 1 | 31 | 19 | 61.29 |
|  | 2 | 31 | 21 | 67.74 |
|  | 3 | 38 | 23 | 60.53 |
|  | 4 | 30 | 19 | 63.33 |
|  | Total | 130 | 82 | 63.22 |
| 0.4 | 1 | 26 | 13 | 50.00 |
|  | 2 | 23 | 10 | 43.48 |
|  | 3 | 32 | 12 | 37.50 |
|  | 4 | 28 | 9 | 32.14 |
|  | Total | 109 | 44 | 40.78 |
| 0.2 | 1 | 30 | 10 | 33.33 |
|  | 2 | 28 | 10 | 35.71 |
|  | 3 | 35 | 12 | 34.29 |
|  | 4 | 38 | 12 | 31.58 |
|  | Total | 131 | 44 | 33.73 |
| 0.1 | 1 | 34 | 8 | 23.53 |
|  | 2 | 44 | 10 | 22.73 |
|  | 3 | 36 | 9 | 25.00 |
|  | 4 | 28 | 8 | 28.57 |
|  | Total | 142 | 35 | 24.96 |
| 0.05 | 1 | 20 | 3 | 15.00 |
|  | 2 | 29 | 5 | 17.24 |
|  | 3 | 31 | 5 | 16.13 |
|  | 4 | 26 | 4 | 15.38 |
|  | Total | 106 | 17 | 15.94 |
| 0 | 1 | 37 | 2 | 5.41 |
|  | 2 | 38 | 1 | 2.63 |
|  | 3 | 29 | 0 | 0.00 |
|  | 4 | 34 | 2 | 5.88 |
|  | Total | 138 | 5 | 3.48 |

TABLE 4

Indoor toxicity test results of 3 test medicaments for *Myzus persicae* Sulzer (48 h)

| Medicament number | Regression equation | $R^2$ | $LC_{50}$ (mg/L) | 95% confidence limit (mg/L) |
|---|---|---|---|---|
| B4 | Y = 4.1809 + 1.6511X | 0.9914 | 3.1342 | 2.6614-3.7119 |
| C4 | Y = 4.9177 + 1.9750X | 0.9820 | 1.1007 | 0.8743-1.3247 |
| A4 | Y = 5.4829 + 1.3508X | 0.9755 | 0.4390 | 0.3655-0.5406 |

Test results (Table 3-1 to Table 3-3, and Table 4) show that 48 h after administration, the $LC_{50}$ of the 3 test medicaments B4, C4 and A4 for aphids was 3.1342 mg/L, 1.1007 mg/L and 0.4390 mg/L respectively.

Conclusion: The $LC_{50}$ value of the A4 for *Myzus persicae* Sulzer was only 40/100 of the $LC_{50}$ value of the C4 for *Myzus persicae* Sulzer, and was 14/100 of the $LC_{50}$ value of the B4 for *Myzus persicae* Sulzer, so the A4 has the highest toxicity to *Myzus persicae* Sulzer.

Although the specific implementations of the disclosure have been described above with reference to the accompanying drawings, they do not limit the scope of protection of the disclosure. On the basis of the technical solution of the disclosure, various modifications or variations that can be made by those skilled in the art without the need for creative labor are still within the scope of protection of the disclosure.

What is claimed is:

1. A naphthalene isoxazoline compound, or a chiral monomer or mixture thereof, or a cis-trans isomer monomer or mixture thereof, or an agrichemically acceptable salt, hydrate or solvate thereof, wherein the compound is 4-(5-(3-chloro-5-(trifluoromethyl)phenyl)-5-(trifluoromethyl)-4,5-dihydroisoxazol-3-yl)-N-((methoxylimino)methyl)-1-naphthylformamide, and has the structure shown in Formula (I):

Formula (I)

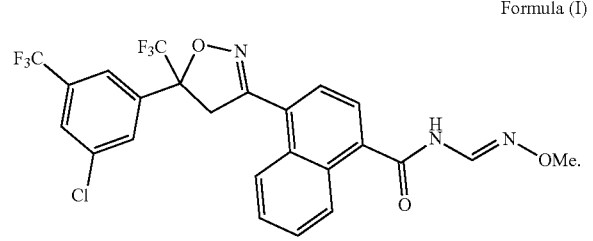 [SMILES: CO/N=C/NC(=O)c1ccc(C2=NOC(c3cc(Cl)cc(C(F)(F)F)c3)(C(F)(F)F)C2)c2ccccc12]

2. A method of preparing an insecticide or acaricide comprising combining the naphthalene isoxazoline compound, or the chiral monomer or mixture thereof, or the cis-trans isomer monomer or mixture thereof, or the agrichemically acceptable salt, hydrate or solvate thereof according to claim 1 with a pesticide formulation auxiliary component.

3. The method according to claim 2, wherein the insecticide or acaricide is effective for killing pests and/or pest mites in food crops, fiber crops, sugar crops, oil crops, beverage crops, vegetable crops, root and stem crops, fruit crops, dried fruit crops, legume crops, melon crops, flower crops, medicinal crops, industrial raw material crops, green manure and forage crops.

4. The method according to claim 2, wherein the insecticide or acaricide is effective for prevention and control of pests and/or pest mites.

5. A pharmaceutical composition comprising the naphthalene isoxazoline compound, or the chiral monomer or mixture thereof, or the cis-trans isomer monomer or mixture thereof, or the agrichemically acceptable salt, hydrate or solvate thereof according to claim 1.

6. A method of preparing an insecticide or acaricide comprising combining the pharmaceutical composition according to claim 5 with a pesticide formulation auxiliary component.

7. An insecticide or acaricide comprising an effective component, wherein the effective component is the naphthalene isoxazoline compound, or the chiral monomer or mixture thereof, or the cis-trans isomer monomer or mixture thereof, or the agrichemically acceptable salt, hydrate or solvate thereof according to claim 1.

8. The insecticide or acaricide according to claim 7, wherein the insecticide or acaricide is prepared into a dosage form by combining the effective component with pesticide formulation auxiliary components suitable in pesticides.

9. An insecticide or acaricide, comprising the pharmaceutical composition according to claim 5.

10. The insecticide or acaricide according to claim 9, wherein the insecticide or acaricide is prepared into a dosage form by combining the pharmaceutical composition with pesticide formulation auxiliary components suitable in pesticides.

* * * * *